United States Patent [19]

Allen, Jr. et al.

[11] Patent Number: 4,497,914

[45] Date of Patent: Feb. 5, 1985

[54] BREATHABLE OSTOMY GASKET COMPOSITION

[75] Inventors: Douglas Allen, Jr., Belle Mead; Eric Flam, East Brunswick, both of N.J.

[73] Assignee: C. R. Bard, Inc., Murray Hill, N.J.

[21] Appl. No.: 398,913

[22] Filed: Jul. 16, 1982

[51] Int. Cl.³ .............................................. C08L 75/04
[52] U.S. Cl. ................................ 523/105; 521/109.1; 523/111; 523/121; 524/732; 524/733
[58] Field of Search ....................... 523/105, 111, 121; 524/732, 733; 521/109

[56] References Cited

U.S. PATENT DOCUMENTS

| | | | |
|---|---|---|---|
| 3,586,648 | 6/1971 | Sambeth et al. | 521/109 |
| 4,011,871 | 3/1977 | Taft | 128/284 |
| 4,181,637 | 1/1980 | Busch et al. | 524/733 |

Primary Examiner—Maurice J. Welsh
Attorney, Agent, or Firm—Dennison, Meserole, Pollack & Scheiner

[57] ABSTRACT

Disclosed is a new breathable ostomy gasket composition derived from the non-aqueous reaction of a polyisocyanate and a polyoxyalkylene polyol moiety having a hydrophilic filler incorporated within the polyol moiety prior to the reaction of the polyisocyanate and the polyol.

12 Claims, No Drawings

BREATHABLE OSTOMY GASKET COMPOSITION

BACKGROUND OF THE INVENTION

This invention relates to ostomy gasket compositions having the unique ability of providing necessary and desirable properties for gasket applications, i.e., breathability, tack, resistance to leakage, dissolution, and disintegration by fluids, and cohesive strength. More particularly, the invention relates to a gasket composition which may be formed as a pad for application to the skin, or as a sealing gasket for an ostomy appliance.

Ostomy appliance pads based upon the inclusion of Karaya powder, as disclosed in U.S. Pat. No. 3,302,647, are currently in general use. Karaya has certain disadvantages since it is a nutrient substance and capable of supporting the growth of micro-organisms, not only in use, but when contaminated in storage prior to use. Karaya compositions are lacking in cohesiveness, and therefore tend to disintegrate as well as become slippery when wet often times necessitating the use of a special adhesive to prevent dislocation from the ostomy site.

In U.S. Pat. No. 4,160,076, there is disclosed hydrophilic foams prepared from a capped polyoxyalkylene polyol reactant having a defined average reaction functionality greater than 2, an aqueous reactant and a carefully balanced combination of a nonionic surface-active agent and a liquid defoaming agent. The resultant foams are characterized by a majority of large size cells and membranes which themselves are formed with small cells. In addition, large amounts of many water-soluble or water-dispersable materials such as cellulosic pigments, dyes, enzymes or the like may be added to the aqueous reactant. By homogeneously distributing these materials in the aqueous reactant they may be distributed throughout the finally prepared foam. However, the large cell size and membranes characteristic of the hydrophilic polyurethane sponges do not possess the necessary properties of tack, elasticity, sealability and flexability needed in an ostomy gasket.

An ostomy gasket possessing varying degrees of tackiness, lubricity, and softness is disclosed in U.S. Pat. No. 3,980,084. The polymeric ostomy sealing gasket therein disclosed in formed by the polymerization of a hydroxyalkyl acrylate or methacrylate in the presence of a polyalkylene glycol, reducing agent, or chain terminator, and water. In manufacturing the gaskets, it is essential that the polymerization reaction be carried out in the presence of water. In this manner, a considerable quantity of water is absorbed into the polymer matrix during the polymerization reaction. In addition, natural or synthetic gums or cellulosic type materials to increase absorptive capacity may be incorporated into the polymer matrix. However, the material disclosed has a very low elongation at break and will not return to its original shape after deformation. In addition the materials are often highly viscous and therefore lack the sealability preferred for use in an ostomy device which may result in leakage around the ostomy seal.

OBJECTS OF THE INVENTION

One object of the invention is realized by providing a polymeric composition adapted for use in contact with the skin derived from the non-aqueous reaction of a polyisocyanate and a polyoxyalkylene polyol moiety having a hydrophilic filler physically incorporated within the polyol prior to the reaction.

Another object of the invention is found in the physical characteristics of the polymeric composition of the present invention, which composition provides a seal between the ostomy device and skin (epidermis) of the human body having a high degree of tack, elasticity, flexibility, and resistance to body fluids. This precludes movement of the seal around the stomal opening which can result in leakage of body material thereby causing irritation and excoriation if allowed to come into repeated or continuous contact with the skin.

Another object of the invention is to the cohesive conformability of the new composition. This property enables the composition to be molded in preferred shapes which inherently adheres to both the patient's skin and the collection receptacle without the use of additional adhesives. The new composition is soft and resilient, minimizing discomfort to the wearer of an ostomy appliance.

Yet another object of the invention is to extend the shelf life and resistance to contamination of the new composition over Karaya products which have a limited shelf life and harden during storage.

SUMMARY OF THE INVENTION

A sealing pad or gasket formed of the composition of this invention is interposed between the face plate of the ostomy device and the skin of the user surrounding the stoma. The sealing pad serves to contain the waste fluids that are highly irritating to the skin and which contain microorganisms of the intestinal tract, and which also give off offensive odors. Additionally, the sealing pad assists in retaining the appliance in place and makes the appliance more comfortable to wear.

The sealing pad of the invention is especially adapted for performing the foregoing functions. Owing to its composition, the pad may be cast in any desirable configuration, and it will retain its shape and not break apart in use.

The composition for forming the pad or gasket is prepared by the reaction of an organic polyisocyanate with one or more di or polyfunctional hydroxyl compounds for example polyoxyalkylene polyols such as those derived from propylene or ethylene oxide, preferably having equivalent weights of at least 500. A hydrophilic filler, such as a cellulosic or natural gum, is incorporated into the polyol moiety of the urethane system prior to the reaction of the polyols with the polyisocyanate moiety.

The soft polymeric matrix or adhesive composition that is formed by the reaction physically encapsulates the uniformly dispersed hydrophilic filler within the resulting self-sustaining adhesive composition. Thus, the product resists swelling and dissolution by or passage of bodily fluids while being inherently breathable thereby readily allowing migration and transfer of gases such as water vapor.

DETAILED DESCRIPTION OF THE INVENTION

The polyisocyanates used in preparing the compositions of the present invention are represented by the formula R(NCO)n where n is at least 2, and R is selected from the group consisting of aliphatic, alicyclic, aliphatic-alicyclic, aromatic or aliphatic-aromatic hydrocarbon compounds.

Examples of commercially available polyisocyanates which may be used include liquid isocyanates or polymeric isocyanates based on 4,4' methyldiphenyldiisocyanates such as UpJohn Company Isonate 143L, UpJohn Company PAPI 901, Mobay Chemical Corporation Mondur CD, and Mobay Chemical Corporation Mondur MRS-10.

Among the commercially available polyoxyalkylene polyols which may be utilized in the practice of the invention are, for example, Niax Polyol-PPG-3025 (Union Carbide Corporation), Poly-G 55-37 (Olin Chemicals), Poly-G 85-28 (Olin Chemicals), and Multranol 3901 (Mobay Chemical Corporation).

The preferred polyols are Union Carbide Niax Polyol-PPG-3025 and Mobay Multranol 3901. The preferred polyisocyanate is UpJohn Company Isonate 143L.

The proportions and molecular weights of the polyoxyalkylene polyols used, as well as the amounts of the hydrophilic fillers, are governed by the desired characteristics of the final product. Thus, one may tailor products having a diverse range of properties such as tackiness, breatheability, cohesiveness and the like.

For example, an elastomer matrix composition formed with diol moieties having nominal equivalent weights of 1500 and triol moieties having nominal equivalent weights of 2000, used in a ratio of approximately 4 to 1 (by equivalents) of diol to triol, yields a particlarly desirable product for an ostomy sealing gasket having physically incorporated therein a hydrophilic filler such as hydroxyethylcellulose, hydroxypropyl cellulose or mixtures thereof in the range of approximately 20 to 35% by weight of the final plastic composition.

It has been found that substantially more breathable products are obtained with the use of hydroxyethylcellulose and hydroxypropylcellulose than, for example, with sodium carboxymethylcellulose, karaya gum or polyacrylamide based polyelectrolytes.

In making the breatheable elastomeric materials of this invention, the polyol moieties are blended with the hydrophilic filler or fillers to form a homogenous mixture, the consistency of which may vary from a thin cream to a paste. The mixture is then reacted with the polyisocyanate moiety. Techniques such as a one-shot or prepolymer reaction procedure may be employed.

In the prepolymer reaction procedure, the polyol moiety is reacted with an isocyanate to yield longer chains having terminal NCO groups which may later react with additional polyol moieties. This defines in part the physical characteristics of the resulting plastic composition.

For example, the elastomeric matrix product tends to become harder and less conformable as the cross-link density of the structure increases, as for example, with higher functionality polyol and/or NCO moieties. These physical characteristics also are evident if the molecular weight of the polyol moiety is decreased. The reverse is true, in that as the molecular weight of the polyol moiety is increased, the composition tends to become softer and weaker.

In addition, the stoichiometry affects the final composition as follows. When the NCO/OH ratio is increased, there is a reduction in conformability and tack, while a decrease in the NCO/OH ratio yields a product with increased tack, but decreased strength.

The reaction is catalyzed by known catalysts for such reactions. Suitable catalysts include organic tin esters such as dibutyltindilaurate, tertiary amines, and other catalysts well known in the art.

In addition, a suitable surfactant, such as Dow Corning Antifoam B may be utilized to aid in controlling the uniformity of flow and formation of the resulting plastic compositions.

Many suitable adhesive compositions can be obtained by minor variations in the amounts of ingredients employed. The following examples are illustrative of the invention.

EXAMPLE #1

35.0 grams (0.0233 equivalents) of Union Carbide Niax Polyol PPG 3025 (1500 Equivalent Weight polyether diol) and 11.0 grams (0.0055 equivalents) of Mobay Multranol 3901 (2000 EW polyether triol) were blended with 2 drops of M & T Chemical Catalyst T-12 (dibutyltindilaurate) and 1 drop Dow Corning Antifoam B (silicone surfactant). To this mixture, 24.0 grams of Hercules Natrosol 250 HHR hydroxyethylcellulose were blended to form a smooth, homogeneous, creamy liquid.

Then, 4.2 grams (0.0292 equivalents) of Upjohn Isonate 143L (liquid isocyanate based on 4, 4' methyldiphenyldiisocyanate) were added and the mixture thoroughly blended for 60–90 seconds, after which it was poured into an open ⅛" deep sheet mold constructed from silicon release paper. The mixture was allowed to cure until set at room temperature for 1 hour and then cured overnight at 45° C.

The resulting product was a soft, flexible, tacky elastomer that is light tan in color and possesses high elasticity and conformability. It is breatheable and highly durable to body fluids. This combination of properties is ideally suited for use as an ostomy barrier.

EXAMPLE #2

The procedure of Example 1 is repeated, except that the silicone surfactant was deleted. The resulting product was identical to that of Example 1.

EXAMPLE #3

The procedure of Example 1 was repeated using 28.8 grams (0.0192 equivalents) of PPG 3025 and 19.2 grams (0.0096 equivalents) of Multranol 3901.

The resulting product was similar to Example 1, however somewhat lower in tack and elasticity.

EXAMPLE #4

The procedure for Example 1 was repeated using 21.6 grams (0.0144 equivalents) of PPG 3025 and 28.8 grams (0.0144 equivalents) of Multranol 3901.

The resulting product possessed less tack and elasticity than Example 3.

EXAMPLE #5

The procedure for Example 1 was repeated using 43.2 grams (0.0288 equivalents) of PPG 3025 and no Multranol 3901 with 40 drops of catalyst T-12.

The resulting product was highly tacky and soft, exhibiting creep, and not suitable for an ostomy gasket.

EXAMPLE #6

The procedure for Example 1 was repeated using no PPG 3025 and 57.6 grams (0.0288 equivalents) of Multranol 3901.

The resulting product tears easily and has low conformability and tack rendering it unsuitable as an ostomy gasket.

EXAMPLE #7

The procedure for Example 1 was repeated using 36.4 grams (0.0243 equivalents) of PPG 3025 and 9.0 grams (0.0045 equivalents) of Multranol 3901.

The resulting product was very soft and tacky exhibiting a slight tendency to creep.

EXAMPLE #8

The procedure for Example 1 was repeated using 11.7 grams (0.0233 equivalents) of Quaker Oats Polymeg 1000 (500 EW polytetramethylene ether glycol) and 11.0 grams (0.0055 equivalents of Multranol 3901.

The resulting product had lower conformability, tack, elasticity, and tear strength than Example 1.

EXAMPLE #9

The procedure for Example 1 was repeated using 13.0 grams Hercules Klucel HF hydroxypropylcellulose in place of Natrosol.

The resulting product was whiter than but otherwise similar to Example 1.

EXAMPLE #10

The procedure for Example 1 was repeated using 16.0 grams Natrosol 250 HHR and 8.0 grams Klucel HF.

The resulting product was lighter colored than Example 1 but otherwise similar in properties.

EXAMPLE #11

The procedure for Example 1 was repeated using an initial cure at 45° C. for 15 minutes to set the material followed by overnight cure at room temperature.

The resulting product is similar to Example 1.

EXAMPLE #12

A prepolymer was prepared by mixing 35.0 grams (0.0233 equivalents) of PPG 3025 with 11.0 grams (0.0055 equivalents) of Multranol 3901 and drying the mixture at 100°–110° C. under vacuum at 30 in. Hg.

8.4 grams (0.0584 equivalents) of Isonate 143L were added slowly with thorough mixing and the mixture maintained at 95° C. for 4 hours under nitrogen with frequent mixing. It was then set aside under a nitrogen lid at room temperature until the following day, when a homogeneous mixture of:

35.0 grams (0.0233 equivalents) of PPG 3025,
11.0 grams (0.0055 equivalents) Multranol 3901,
4 drops of T-12 (dibutyltindilaurate),
2 drops antifoam B, and
48.0 grams Natrosol 250 HHR was added. The mixture was thoroughly blended for 60–90 seconds and poured into a sheet mold as in Example 1, cured at room temperature for 1 hour and then at 45° C. overnight.

The resulting product was identical to Example 1.

EXAMPLE 13

A quasi-prepolymer was prepared by mixing 10 grams (0.0694 equivalents) of Isonate 143L into 10 grams (0.0066 equivalents) of PPG 3025 (previously dried at 100°–110° C. under vacuum at 30 in. Hg.). The mixture was maintained under nitrogen at 95° C. for 4 hours with frequent mixing, after which it was set aside under a nitrogen lid at room temperature until the following day.

At that time, 8.4 grams of the quasi-prepolymer were added to a homogeneous mixture consisting of the following:

30.8 grams (0.0205 equivalents) PPG 3025
11.0 grams (0.0055 equivalents) Multranol 3901
4 drops T-12
2 drops Antifoam B
24.0 grams Natrosol 250 HHR The mixture was thoroughly blended for 60–90 seconds and poured into a sheet mold as in Example 1, cured at R.T. for 1 hour, then at 45° C. overnight.

The resulting product was identical to Example 1.

We claim:

1. A polymeric composition, for providing an elastomeric adhesive, breatheable, cohesive, conformable, body fluid generally non-degradable shaped ostomy gasket for use in adherent contact with the skin, which comprises a product derived from the generally non-aqueous reaction of an organic polyisocyanate, and a polyoxyalkylene polyol moiety comprising a mixture of a major portion of polyol having a diol functionality and a minor portion of polyol of at least triol functionality, and having incorporated into the polyol moiety prior to the generally non-aqueous reaction of the polyisocyanate and the polyol moiety a hydrophilic filler wherein there is provided a polymeric matrix characterized by the physical encapsulation of the hydrophilic filler within the polymeric matrix.

2. A polymeric composition, for providing an elastomeric adhesive, breatheable, cohesive, conformable, body fluid generally non-degradable shaped ostomy gasket for use in adherent contact with the skin which comprises a product derived from the generally non-aqueous reaction of an organic polyisocyanate of the formula $$R(NCO)_n$$

where R is selected from the group consisting of aliphatic, alicyclic, aliphatic-alicyclic, and aromatic or aliphatic-aromatic hydrocarbon compounds and n is at least 2, and a polyoxyalkylene polyol moiety of the formula $$[R(OH)_n]R(OH)_{n'}$$

where R is a polyoxyalkylene and n' is at least 2, the polyol moiety comprising a mixture of a major portion of polyol having a diol functionality and a minor portion of polyol of at least triol functionality, and having incorporated into the polyol moiety prior to the reaction of the polyisocyanate and the polyol moiety, a hydrophilic filler wherein there is provided a polymeric matrix characterized by the physical encapsulation of the hydrophilic filler within the polymeric matrix.

3. A polymeric composition as defined in claim 1 wherein said polyol moiety consists of diols of nominal equivalent weights of 1500 and triols of nominal equivalent weights of 2000 in a ratio of approximately 4 to 1 of diol to triol.

4. A polymeric composition in accordance with claim 1 in which:
said polyisocyanate is a liquid isocyanate comprising 4,4' methyldiphenyldiisocyanate;

said polyol moiety is a mixture of 1500 equivalent weight polyether diol and 2000 equivalent weight polyether triol.

5. A process for making a polymeric composition, for providing an elastomeric adhesive, breatheable, cohesive, conformable, body fluid generally non-degradable shaped member for use as an ostomy appliance seal in adherent contact with the skin which comprises reacting under generally non-aqueous conditions an organic polyisocyanate and a polyoxyalkylene polyol moiety comprising a mixture of a major portion of polyol having a diol functionality and a minor portion of polyol of at least triol functionality, and having incorporated into the polyol moiety prior to the general non-aqueous reaction of the polyisocyanate and the polyol a hydrophilic filler wherein there is produced a polymeric matrix characterized by the physical encapsulation of the hydrophilic filler within the polymeric matrix.

6. A process for making a polymeric composition, for providing an elastomeric adhesive, cohesive, conformable, body fluid generally non-degradable shaped member for use as an ostomy appliance seal in adherent contact with the skin which comprises reacting under generally non-aqueous conditions an organic polyisocyanate of the formula $$R(NCO)_n$$

where R is selected from the group consisting of aliphatic, alicyclic, aliphatic-alicyclic, and aromatic or aliphatic-aromatic hydrocarbon compounds and n is at least 2, and a polyoxyalkylene polyol moiety of the formula $$[R(OH)_n]R(OH)_{n'}$$

where R is a polyoxyalkylene and n' is at least 2, the polyol moiety comprising a mixture of a major portion of polyol having a diol functionality and a minor portion of polyol of at least triol functionality, and having incorporated into the polyol moiety prior to the reaction of the polyisocyanate and the polyol moiety, a hydrophilic filler wherein there is produced a polymeric matrix characterized by the physical encapsulation of the hydrophilic filler within the polymeric matrix.

7. A process as defined in claim 6 wherein said polyol moiety consists of diols of nominal equivalent weight of 1500 and triols of nominal equivalent weights of 2000 in a ratio of approximately 4 to 1 of diol to triol.

8. A polymeric composition in accordance with claim 6 in which:
    said polyisocyanate is a liquid isocyanate based on 4,4' methyldiphenyldiisocyanate;
    said polyol moiety is a mixture of 1500 equivalent weight polyether diol and 2000 equivalent weight polyether triol.

9. An ostomy appliance seal produced by the process of claim 5.

10. An ostomy appliance seal produced by the process of claim 6.

11. An ostomy appliance seal produced by the process of claim 7.

12. An ostomy appliance seal produced by the process of claim 8.

* * * * *